United States Patent [19]
Mears

[11] Patent Number: 6,042,591
[45] Date of Patent: Mar. 28, 2000

[54] MOVABLE LIGATING BAND DISPENSER AND METHOD

[75] Inventor: Eric L. Mears, Duluth, Ga.

[73] Assignee: Ensurg, Inc., Norcross, Ga.

[21] Appl. No.: 09/062,281

[22] Filed: Apr. 17, 1998

[51] Int. Cl.⁷ .................................................. A61B 17/00
[52] U.S. Cl. ............................................................... 606/140
[58] Field of Search ........................ 606/140, 139, 606/141, 135, 158, 151, 148

[56] References Cited

U.S. PATENT DOCUMENTS

| | | | |
|---|---|---|---|
| 3,760,810 | 9/1973 | Van Hoorn . | |
| 3,911,923 | 10/1975 | Yoon . | |
| 4,226,239 | 10/1980 | Polk et al. . | |
| 4,257,419 | 3/1981 | Göltner et al. . | |
| 4,990,152 | 2/1991 | Yoon ........................................ | 606/140 |
| 5,207,690 | 5/1993 | Rohrabacher et al. .................. | 606/135 |
| 5,269,789 | 12/1993 | Chin et al. .............................. | 606/140 |
| 5,308,353 | 5/1994 | Beurrier . | |
| 5,320,630 | 6/1994 | Ahmed .................................... | 606/140 |
| 5,356,416 | 10/1994 | Chu et al. ................................ | 616/140 |
| 5,398,844 | 3/1995 | Zaslavsky et al. ....................... | 221/208 |
| 5,462,559 | 10/1995 | Ahmed .................................... | 606/140 |
| 5,507,797 | 4/1996 | Suzuki et al. ............................ | 606/140 |
| 5,569,268 | 10/1996 | Hosoda .................................... | 606/140 |
| 5,624,453 | 4/1997 | Ahmed .................................... | 606/140 |
| 5,681,328 | 10/1997 | Lamport et al. ......................... | 606/140 |
| 5,697,940 | 12/1997 | Chu et al. ................................ | 606/140 |
| 5,735,861 | 4/1998 | Peifer et al. ............................. | 606/139 |
| 5,788,715 | 8/1998 | Watson, Jr. et al. ..................... | 606/140 |

FOREIGN PATENT DOCUMENTS

| | | |
|---|---|---|
| 0310582 | 4/1989 | European Pat. Off. . |
| 0679368 | 11/1995 | European Pat. Off. . |
| 96024292 | 8/1996 | WIPO . |

OTHER PUBLICATIONS

Directions for Use Brochure for Speedband™ Multiple Band Ligator, Microvasive Boston Scientific Corporation, pp. 1–8, 1995.

*Primary Examiner*—Michael Buiz
*Assistant Examiner*—Vikki Trinh
*Attorney, Agent, or Firm*—Sidley & Austin

[57] ABSTRACT

A ligating band dispenser capable of retraction during movement and exploration to offer an unimpaired field of view for an image sensing device of a hosting endoscope as well as extension to facilitate a conventional ligating procedure. Actuating the ligating band dispenser is accomplished with an actuating mechanism that includes a controller to enable a user to selectively dispense one or more ligating bands and/or retract/extend the dispenser.

48 Claims, 7 Drawing Sheets

MOVABLE LIGATING BAND DISPENSER AND METHOD

FIELD OF THE INVENTION

The present invention relates to a movable ligating band dispenser, and in particular, to a movable ligating band dispenser which assumes a retracted position, providing greater mobility and an unimpaired field of view for an image sensing device of a hosting endoscope or laparoscope, and an extended position, for enabling a conventional ligating procedure.

BACKGROUND OF THE INVENTION

Ligation is a medical procedure in which an elastic band, or ligating band, is placed about tissue to prevent fluid flow therethrough. Where a ligating band is placed about, for example, a ballooning varix, polyp, hemorrhoid, or pre-cancerous lesion, a contracted ligating band induces fusion and healing in the base tissue and subjects the ligated tissue to necrosis. The necrotic tissue eventually separates from the surrounding tissue and passes into the human system. Alternatively, ligation may also be used for purposes of sterilization, wherein a ligating band may be placed over a folded loop portion of a Fallopian tube or a vas deferens to prevent the passage of internal reproductive fluids.

Means for delivering ligating bands, or ligating band dispensers, take various forms. One such form is a dedicated ligating band dispenser instrument which has a dispensing portion at a distal end, an actuating mechanism at a proximal end, and a typically rigid shaft therebetween. These instruments are useful for ligating tissue in which the user has access to the tissue to be ligated, e.g., tissue exposed through an invasive surgical procedure.

In contrast, ligating band dispensers may be positioned on the distal tip of an endoscope or a laparoscope. An endoscope is a conventional medical device used for viewing, exploring, and delivering therapies to internal regions of a patient. A laparoscope is a specialized endoscope for viewing a patient's peritoneal cavity. Unlike dedicated ligating band dispensing instruments, an endoscope allows minimally invasive intrusion into a patient.

FIGS. 1 and 2 illustrate a conventional endoscope. Endoscope 10 has a control portion 12 and a insertion portion 14 terminating at insertion tip 16. Insertion portion 14 is of such a length to permit access to internal regions of a patient.

FIG. 2 illustrates the face of insertion tip 16. A number of channels extend from the control portion 12 to the insertion tip 16, where the channels terminate in functional outlets 18–26. For the purposes of this example, outlet 18 is a light source; outlet 20 is a wide-field image sensing device, which transmits a video or fiber optic signal to a coupled monitor or eyepiece (not shown) at control portion 12; outlet 22 delivers a stream of water or air for clearing the image receiving device or flushing an internal bodily region; and outlet 24 is an outlet to a working (or biopsy) channel. Inlet 28 of the working channel can be coupled to a suction device or a lavage fluid source (not shown) or can receive various medical instrumentation (not shown) for passage through the working channel and outlet 24. Optional outlet 26, for larger diameter endoscopes, is an outlet for a second working channel. A second working channel allows additional operations in a manner consistent with the working channel described above.

Endoscope ligating band dispensers are fixedly mounted about and protrude from insertion tip 16 of a hosting endoscope, wherein such dispensers carry one or more expanded ligating bands about their outer diameter. Projecting from insertion tip 16, conventional dispensers inherently narrow the field of view of the image sensing device of outlet 20. In an effort to improve such impairment, some conventional devices are fabricated from a transparent material. While such material may facilitate the outward passage of light from outlet 18, such material does not practically improve the field of view for the wide-field image sensing device. Specifically, the use of transparent material commonly induces distortion about the periphery of a displayed image. Distortion is a product of both the curvature of the dispenser and the accumulation of bodily fluids about the outer surface of the dispenser. Ligating bands stored on the outer diameter of these dispensers further obstruct the field of view through the dispenser material.

A conventional endoscope ligating band dispenser is shown in FIG. 3. Dispenser 1000 is capable of dispensing multiple ligating bands 1002, whether individually or sequentially. Typical of the prior art, dispenser 1000 is cylindrical and hollow in nature, where an inner periphery of dispenser 1000 defines a cavity and an outer periphery carries the ligating bands 1002. Dispenser 1000 projects from the distal end of insertion tip 16. Accordingly, dispenser 1000 inhibits the field of view of a wide-field image sensing device (not shown) of the hosting endoscope in accordance with the limitations of conventional devices outlined above.

Conventional dispensers, such as dispenser 1000, increase the length of insertion tip 16. A ligating band dispenser-equipped endoscope is commonly used within a hollow body cavity, for example, an esophagus. Insertion tip 16 must assume almost a 90° bend with respect to the longitudinal axis of the insertion portion 14 to obtain a clear view normal to the inner surface of an esophagus. The additional length of the ligating band dispenser from insertion tip 16 can significantly restrict the motion and flexibility of insertion tip 16 within a hollow body cavity. Accordingly, the added length, coupled with the severely restricted peripheral view, makes the presence of conventional ligating band dispensers an operational liability during the exploration and placement phases of ligation procedures.

SUMMARY OF THE INVENTION

The present invention is directed to a ligating band dispenser capable of being extended and/or retracted from a distal end of an insertion portion of an endoscope. According to one aspect of the present invention, such a dispenser includes a proximal end adapted to be movably received at the distal end of the insertion portion, a distal end, and a sealing member. The sealing member moves relative to the endoscope with movement of the dispensing device and seals a space between the dispensing device and the hosting endoscope.

A dispensing device in accordance with another aspect of the present invention includes a ligating band dispenser adapted to be slidably received on a distal end of an insertion portion of an endoscope. The dispenser has a proximal end, a distal end, and a sealing member to establish a seal between the dispenser and the hosting endoscope. The dispenser sealing member has at least a portion which moves relative to the endoscope with movement of the dispenser. Coupled to the ligating band dispenser, an actuating mechanism selectively effects the movement of the dispenser from a first position to at least a second position.

In operation, the present invention facilitates increased flexibility of motion and a greater field of view for an image sensing device of the hosting endoscope during a ligation procedure. More specifically, steps for ligating tissue may include providing a dispenser on a distal end of an insertion portion of an endoscope, said ligating band dispenser being coupled to a control portion with at least one control filament for selectively moving the dispenser from a retracted position to at least a dispensing position relative to the distal end of the insertion portion. The ligating band dispenser supports one or more expanded ligating bands. The insertion portion, including the dispenser is inserted into a patient, wherein the dispenser is in a retracted position relative to the distal end of the insertion portion. The insertion portion is then navigated to a desired tissue site. Once a tissue site is identified, the at least one control filament is manipulated so as to extend the dispenser to at least a dispensing position. The extended dispenser creates a volume substantially defined by the dispenser sufficient to receive that tissue to be ligated. Application of a suction causes such tissue to be drawn into the volume, whereafter a ligating band is dispensed.

An object of the present invention is to provide an endoscope ligating band dispensing device which enables an improved field of view for an image sensing device of a hosting endoscope.

Another object is to minimize the length in which a ligating band dispenser protrudes from an insertion tip of a hosting endoscope for easier insertion and greater flexibility and mobility during exploration.

Another object of the present invention is to provide an endoscope ligating band dispensing device which may assume a first position for an increased field of view for an image sensing device of a hosting endoscope and may assume a second position for dispensing a ligating band.

Another object of the present invention is to provide a controller and an actuating device for an endoscope ligating band dispensing device to enable the selective retraction/extension of a ligating band dispenser as well as remote, selective ligating band dispensing.

Other objects and advantages of the present invention will be apparent to those of ordinary skill in the art having reference to the following specification together with the drawings.

BRIEF DESCRIPTION OF THE DRAWINGS

Referring now to the drawings in which like reference numerals and letters indicate corresponding elements throughout the several views, if applicable.

DETAILED DESCRIPTION OF THE PREFERRED EMBODIMENTS

Figure 4A:
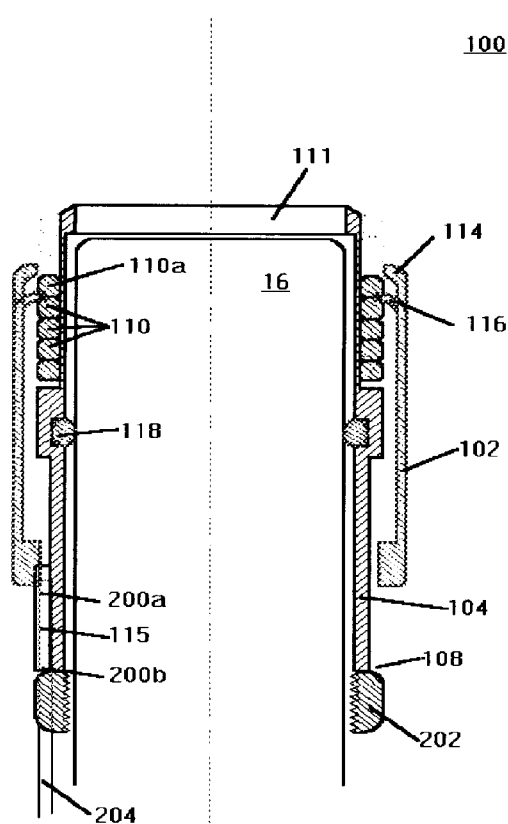
FIGS. 4a through 4c is a partial, sectional view of a movable ligating band dispenser of a first embodiment.
Figure 4B:
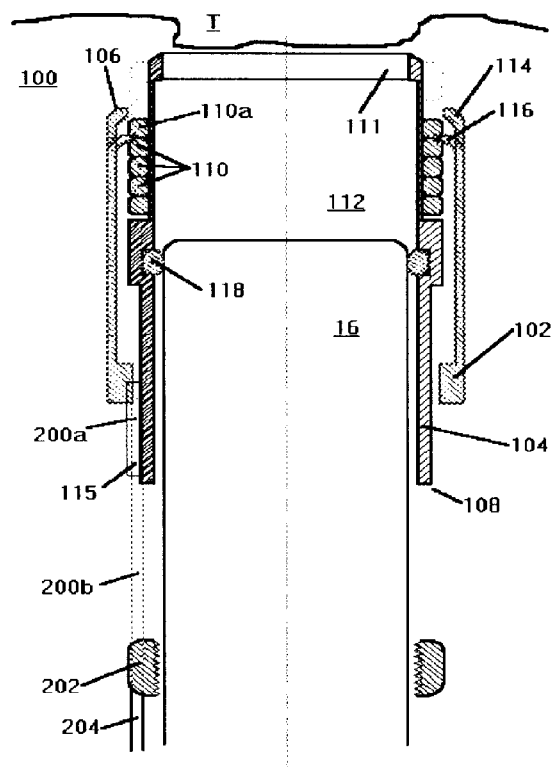
Figure 4C:
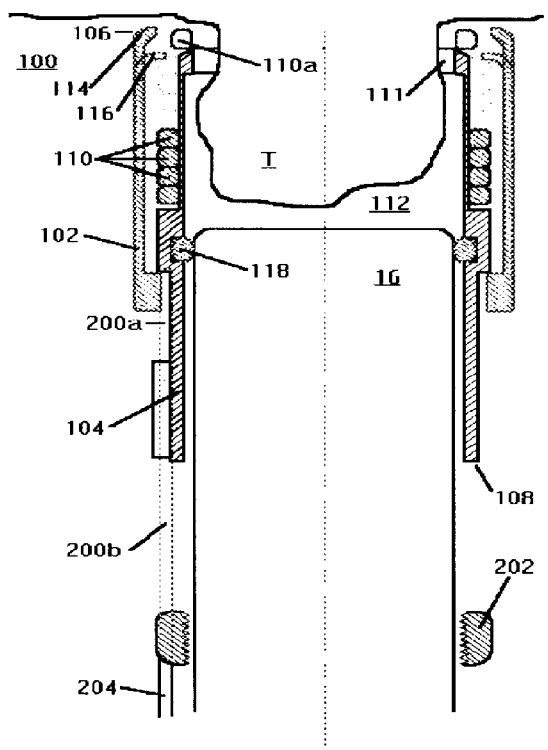

FIGS. 4a through 4c illustrate one embodiment of a movable dispenser 100. Dispenser 100 includes dispensing member (an outer sleeve) 102 slidably received on sleeve 104 (an inner sleeve), sleeve 104 being adapted to fit about insertion tip 16 of a hosting endoscope 10. Both dispensing member 102 and sleeve 104 have a cross-sectional shape consistent with the outer shape of insertion tip 16 of an endoscope 10, wherein such shape is typically circular in nature. Dispensing member 102 and sleeve 104 are constructed of a medical grade material suitable for exposure to a human system and which display low friction characteristics when in contact. Moreover, at least dispensing member 102 may be constructed of a transparent or translucent material to facilitate the passage of light when in an extended position (FIGS. 4b and 4c).

Figure 1:
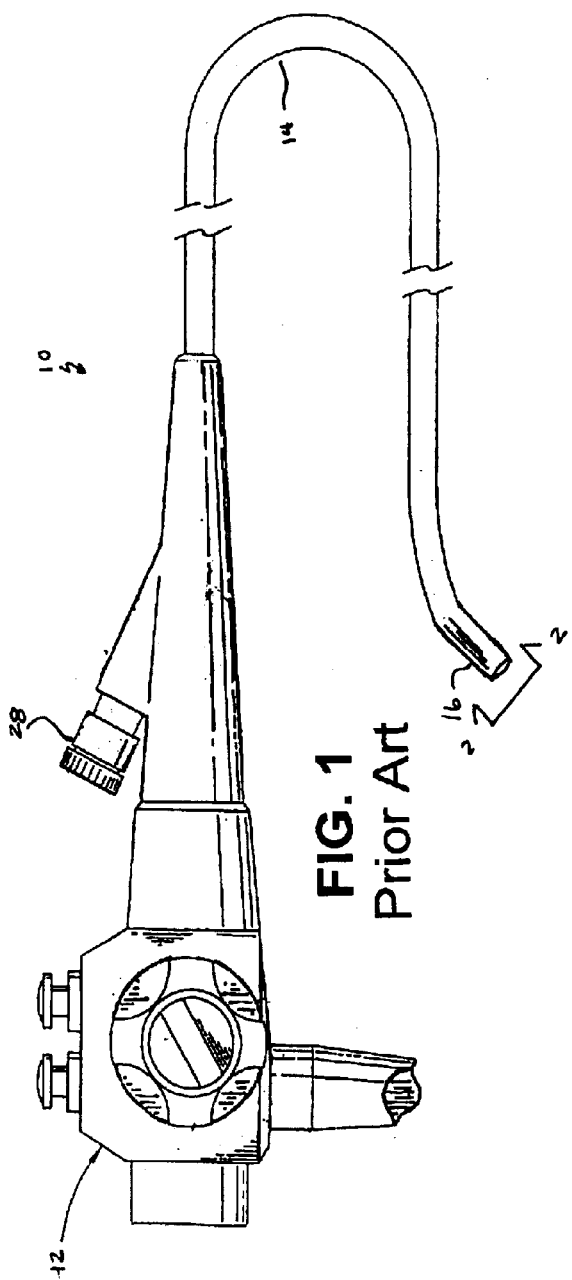
FIG. 1 illustrates a conventional endoscope.
Figure 2:
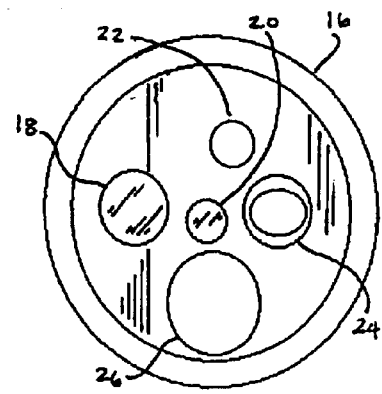
FIG. 2 is a view along line 2—2 of the insertion tip of the endoscope of FIG. 1.
Figure 3:
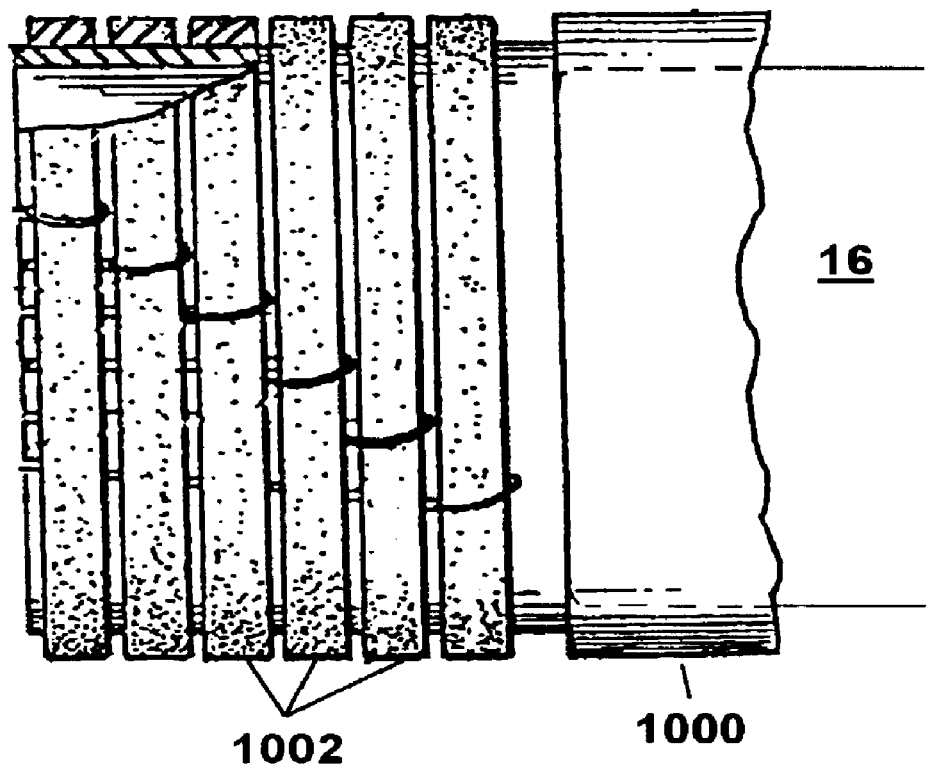
FIG. 3 illustrates a conventional ligating band dispenser.

Referring to FIGS. 4a through 4c, dispenser 100 is generally cylindrical in shape and has a distal end 106 and a proximal end 108. The distal end of sleeve 104 defines opening 111 which has a diameter substantially consistent with the face diameter of insertion tip 16. opening 111 allows use of the functional outlets 18–26 (FIG. 2) of the hosting endoscope, for example, transmission of light, passage of instrumentation, receipt of visual imaging, and the like. Sleeve 104 further includes a region, just proximal to its distal end, which carries at least one expanded ligating band 110. Preferably, sleeve 104 carries a plurality of expanded ligating bands 110.

Dispensing member 102 has a fixed shoulder 114 and a plurality of inwardly-biased, spring fingers 116. The distance between shoulder 114 and the aligned spring fingers 116 is approximately equal to the diameter of a single ligating band 110. To limit undesired rotation of dispensing member 102, dispensing member 102 may include a recess or the like (not shown) along an inner surface to receive a longitudinal protrusion 115 which extends along an outer surface of sleeve 104. Alternatively, protrusion 115 could spiral about sleeve 104 (not shown), to induce a desired rotation, and facilitate a predetermined rate of extension of dispensing member 102 relative to sleeve 104.

Operation of dispenser 100 is illustrated by FIGS. 4a through 4c. FIG. 4a illustrates a first condition in which dispenser 100 is in a retracted position. Once tissue T for ligation is identified, dispenser 100 is extended to a dispensing position (FIG. 4b), thus creating volume 112, substantially defined by an inner surface of sleeve 104, to receive the chosen tissue T. To ready ligating band 110a, dispensing member 102 is drawn proximally until the spring fingers 116 are proximal to the distal-most ligating band 110a (FIG. 4b).

Volume 112 is subjected to a suction to draw tissue T therein (FIG. 4c), or tissue T is physically drawn into volume 112 using forceps (not shown) or the like which are passed through the work channel of endoscope 10 to the distal end 16 of dispenser 100. For dispensing, dispensing member 102, and thus ligating band 110a, are caused to move distally. When dispensing member 102 nears full extension, ligating band 110a is released. Following dispensing of the required number of ligating bands 110, dispenser 100 may again be retracted, and the sequence repeated, if desired.

In a retracted position, it is preferred that the distal end 106 of ligating band dispenser 100 be substantially aligned with the distal end of insertion tip 16. However, because certain ligating band dispensing mechanisms (i.e., those formed substantially along an inner periphery of dispenser 100 within chamber 112) may prevent this preferred position, a "retracted position" means a ligating band dispenser position which enables an improved field of view over a fully extended (or conventional) ligating band dispenser position and/or forms volume 112 insufficient to enable a ligation procedure.

Figure 5:
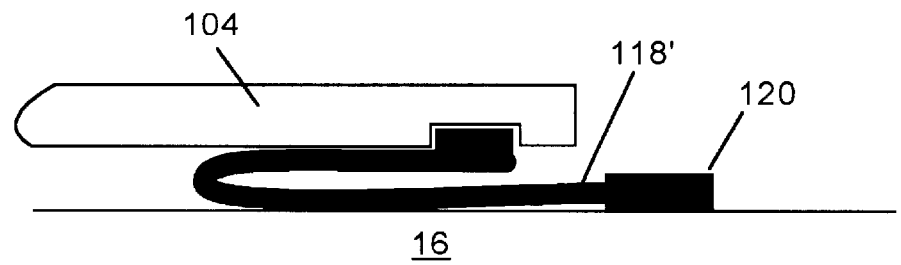
FIG. 5 is a partial, sectional view of a rolling diaphragm seal for an alternative embodiment of at least the movable ligating band dispenser of FIGS. 4a–4c.

As discussed above, a suction may be applied to draw tissue T into volume 112. Necessarily, a seal must be established between the insertion tip 16 of the endoscope 10 and sleeve 102 to efficiently maintain an applied suction. FIGS. 4a–4c show one embodiment of seal 118. More specifically, seal 118 is an o-ring type seal or v-ring, lip-type seal which slidably engages insertion tip 16 throughout the motion of sleeve 104. Seal 118 may also take the form of a rolling diaphragm (FIG. 5). For this embodiment, seal 118' includes a thin membrane coupled to dispensing member 102 and anchored to insertion tip 16. Seal 118' is joined to insertion tip 16 through application of an adhesive or, more preferably, by an integral elastic band 120 which tightly engages endoscope 10. As another alternative, a portion of sleeve 104 at or about proximal end 108 could be constructed of a flexible material which circumferentially extends about insertion tip 16. For this alternative, sleeve 104 can move relative to insertion tip 16 consistent with the above examples; however, when a suction is applied to volume 112 the flexible material is caused to contract about insertion tip 16 to both establish a seal and reduce those forces transmitted to actuating filament 200b due to the tendency of dispenser 100 to retract when the suction is applied.

While the above description sets forth three examples of seal 118, one skilled in the art will appreciate that seal 118 may take any variety of forms. Importantly, however, seal 118 of the present invention maintains a fluid-tight seal when dispenser 100 is at least in an extended position, and at least a portion of seal 118 travels through the extension/retraction motion of dispenser 100.

Dispenser 100 is extended and retracted using an actuating mechanism. An actuating mechanism in accordance with the present invention includes actuating elements 200, which are coupled between dispenser 100 and controller 150, which will be discussed in greater detail below.

FIGS. 4a–4c illustrate one embodiment of actuating elements 200. Actuating elements 200 are preferably semi-rigid filaments or thin cable (collectively "filaments") formed from stainless steel, nitinol, or the like. For this embodiment, actuating filaments 200 are exterior to and extend along the outer surface of insertion portion 14. Actuating filament 200a is coupled to dispensing member 102 and effects movement of the dispensing member 102, while actuating filament 200b is coupled to sleeve 104 to effect retraction/extension of dispenser 100. In operation, distally-directed forces applied to filaments 200a, 200b cause an extension of dispensing member 102 and sleeve 104, respectively, while a proximally-directed force applied to filaments 200a, 200b cause a retraction of the same. In some instances, certain actuating elements 200 can perform multiple tasks to simplify operations, for example, a distally-directed force applied to actuating filament 200b can effect the extension of both members 102, 104 and, when dispenser 100 is extended, a proximally-directed force applied to actuating filament 200b can effect a retraction of both members 102, 104. While these embodiments of actuating element 200 operate in response to the application of axial forces, actuating elements 200 could include features to effect extension/retraction of dispenser 100 and/or dispensing of ligating bands 110 in response to an applied rotation.

Actuating filaments 200a, 200b pass through grasping ring 202. Preferably, ring 202 is an independent elastic band which is positioned proximal of dispenser 100 and tightly holds to the insertion tip 16. Preferably, filaments 200a, 200b are covered with a load bearing encasement 204, which terminates at and is integral with ring 202. Operatively, ring 202 asserts a force against casing 204 which is at least equal and opposing to any distally-directed forces applied to actuating filaments 200a, 200b. Ring 202 may further include securing means to receive and releasably secure sleeve 104 in a retracted position. If not independent, ring 202 can dually serve as the anchor 120 for the rolling diaphragm seal 118' of FIG. 5. For this embodiment, actuating filaments 200a, 200b may be further secured along the length of the insertion portion 14 with tape, adhesive, additional elastic bands, a spiral wrap of actuating filaments 200a, 200b about insertion portion 14, or the like.

FIGS. 6a–6d illustrate other embodiments and combinations of actuating elements 200. Common to these embodiments, however, actuating elements 200 pass through outlet 24 and extend internally through the work channel of insertion portion 14 to inlet 28.

Figure 6A:
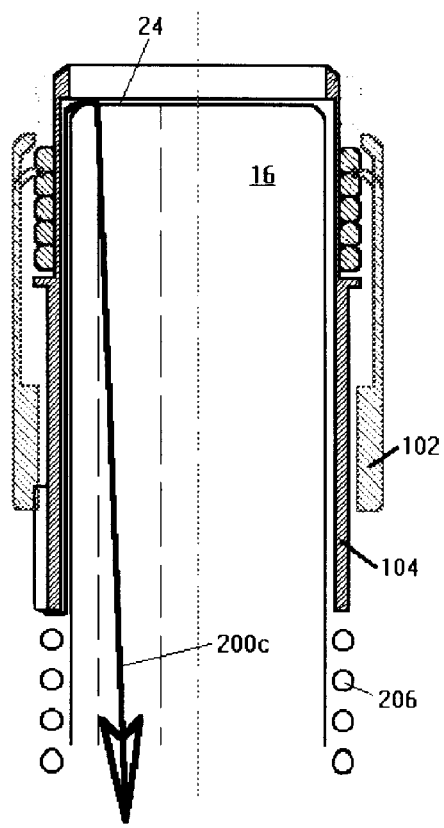
FIGS. 6a and 6b are partial, sectional views of a movable ligating band dispenser of another embodiment.
Figure 6B:
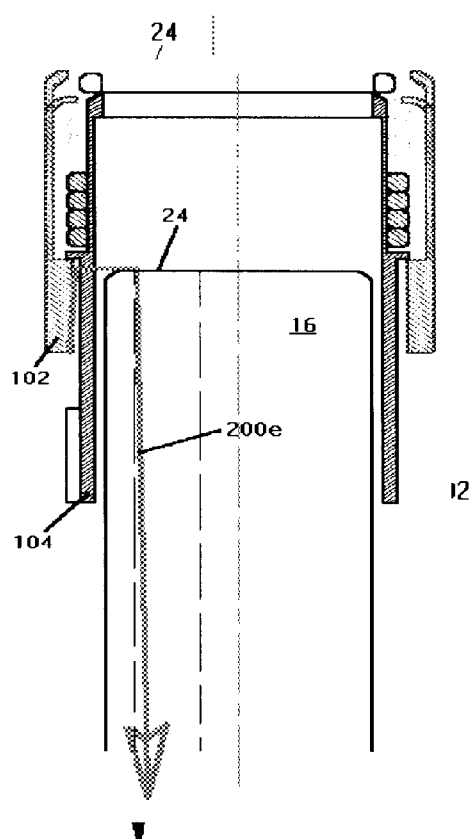

FIG. 6a preferably illustrates dispenser 100 biased proximally by spring 206. Actuating filament 200c is coupled to the proximal end of sleeve 104, and a proximally-directed force applied to filament 200c caused dispenser 100 to be extended. In contrast, FIG. 6b shows a distally-biased dispenser 100 using spring 206. Actuating filament 200c is coupled to the distal end of sleeve 104, and a proximally-directed force applied to filament 200c causes dispenser 100 to be retracted. Rather than a conventional spring, biasing element 206 may assume, for example, an elastic sleeve (not shown) or the like which functions similar to a spring and in a manner described above. For clarity, actuating filaments 200 for dispensing stored ligating bands 110 are not shown in either of these figures.

Figure 6C:
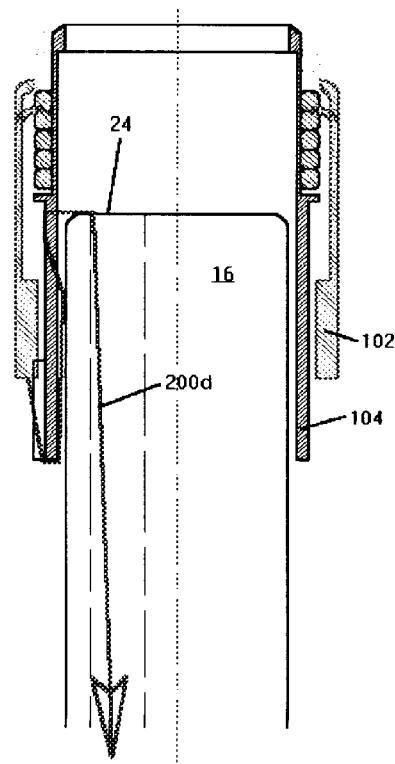
FIG. 6c is a partial, sectional view of a movable ligating band dispenser having an actuating filament.

FIG. 6c illustrates actuating filament 200d to extend sleeve 104 and retract dispensing member 102 to "load" the distal-most ligating band 110a between shoulder 114 and spring fingers 116. Actuating filament 200d is secured at a proximal end of dispensing member 102 and passes around both the proximal end of sleeve 104 and the distal end of insertion tip 16 before entering outlet 24 and the work channel of endoscope 10. Alternatively, if the configurations of either FIG. 6a or FIG. 6b are combined with the configuration illustrated in FIG. 6c, actuating filament 200d is used exclusively for readying a ligating band 110 for dispensing.

Figure 6D:
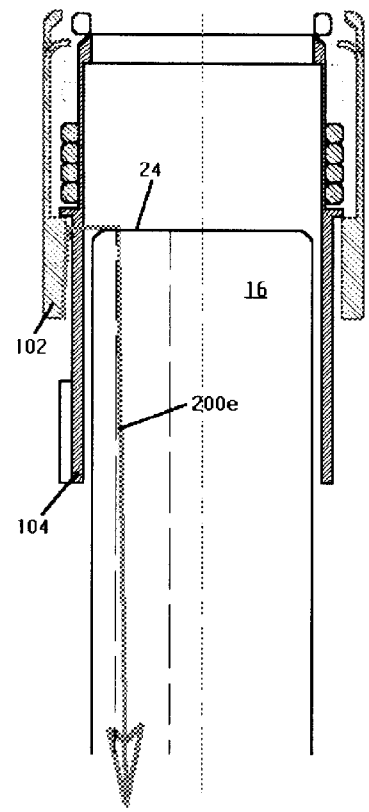
FIG. 6d is a partial, sectional view of a movable ligating band dispenser having an actuating filament.

FIG. 6d illustrates actuating filament 200e which functions to dispense a loaded ligating band 110a. Application of a proximally-directed force to actuating filament 200e causes dispensing member 102 to move distally and dispense ligating band 110a. Actuating filament 200e is secured to the proximal end of dispensing member 102 and passes around the distal end of insertion tip 16 before entering outlet 24 and the work channel extending through endoscope 10.

As actuating filaments 200d, 200e are used to load and dispense each ligating band 110, dispenser 100 of this embodiment will necessarily include both actuating filaments 200d, 200e. Accordingly, actuating filaments 200d, 200e may be independent filaments or portions of a single filament.

While the examples set forth in FIGS. 6a–6d provide specific filament attachment points and other references, one skilled in the art shall appreciate that these attachment points/references are but one set of examples, and that the actuating filaments may be joined at other points of dispenser 100 to effect the movement of dispenser 100 in a manner consistent with the present invention. Moreover, other actuating systems, for example, hydraulic or pneumatic systems (not shown) may also facilitate the extension/retraction of dispenser 100, wherein actuating elements would be fluid tubing (not shown) spanning between a pressurized fluid source and dispenser 100.

Although the above description has been directed to a specific dispenser 100, one skilled in the art shall appreciate that dispenser 100 may have a plurality of configurations, including the modification of conventional dispensers; provided, however, such configurations allow the extension and retraction of the dispenser and/or include a functioning seal that is adapted to move relative to a hosting endoscope through the movement of the dispenser.

Figure 7:
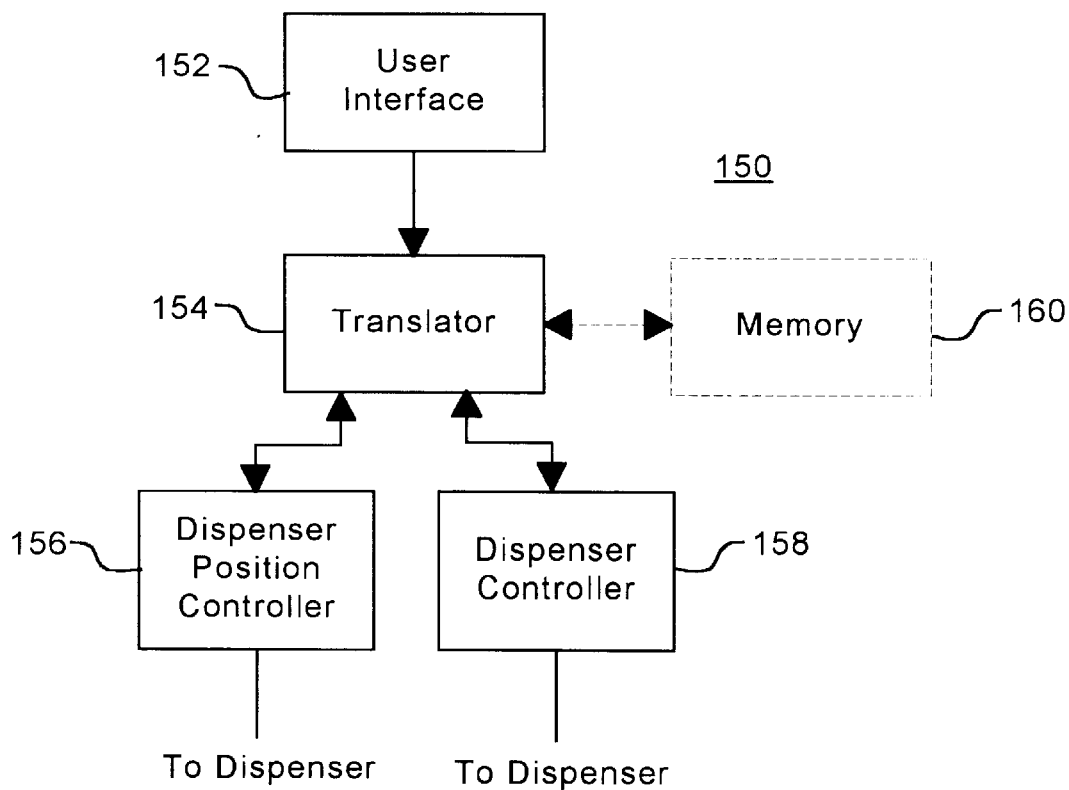
FIG. 7 illustrates one embodiment of an actuating mechanism controller in accordance with the present invention.

As provided above, actuating elements 200 are coupled between dispenser 100 and controller 150. While actuating elements 200 can be manipulated directly (i.e., by hand) by the user, controller 150 enables a user to accurately and selectively control the dispensing of a stored ligating band 110 and/or the movement of dispenser 100. Controller 150 may be rather simple (for example, a filament wrapped-shaft [not shown] having filament portions 200d, 200e extending therefrom, wherein the combined tension on filaments 200d, 200e can effect the extension of dispenser 100 and rotation of the shaft while under tension effects at least the loading and dispensing of ligating band 100a); however, in reference to FIG. 7, controller 150 preferably includes user interface 152, translator 154, dispenser position controller 156, and dispenser controller 158.

User interface 152 has, for example, a push button panel, a selector knob, and/or a control lever to allow a user to input desired instructions to control dispenser 100. Translator 154 receives an indication, whether electrical or mechanical, from user interface 152 and effects the user's instructions via dispenser position controller 156 and dispenser controller 158.

Translator 154 transforms input instructions to effect dispenser 100 movement and/or ligating band 110 dispersal. Depending on whether controller 150 operates mechanically or electro-mechanically, translator 154 may be a central processing unit (CPU), a linear or rotary cam, a linear or rotary shaft, or the like. If translator 154 is a CPU, controller 150 further includes memory 160, which stores programs responsive to user inputs to control the dispenser 100 movement and/or ligating band 110 dispersal. Dispenser position controller 156 and dispenser controller 158 may be pressurized fluid sources, electric motors, solenoids, cams, or the like and are responsive to translator 154 output.

While translator 154 and controllers 156, 158 generally function to move dispenser 100 and cause ligating bands 110 to be dispensed, it is desired that this system further control the actuating forces applied to perform these operations. Application of excessive force could damage dispenser 100 or cause a system malfunction. Accordingly, controller 150 translates user inputs into actuating instructions having prescribed characteristics, for example, actuating distances, applied actuating forces, and/or actuating durations, to prevent damage to dispenser 100 and to ensure systematic and consistent operation of the present invention.

Figure 8:
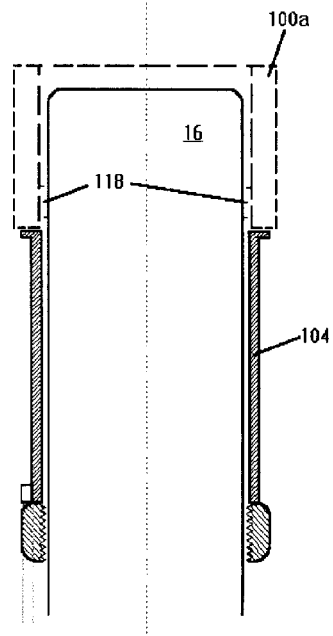
FIG. 8 is a partial, sectional view of a movable ligating band dispenser of another embodiment.

FIG. 8 illustrates another embodiment of the present invention. While platform 104 is consistent and similar to that described above, both in structure and functionality, platform 104 does not directly support one or more ligating bands 110. Rather, platform 104 includes a region, proximal to its distal end, which engages a conventional-type ligating band dispenser 100a or any one of the ligating band dispensing devices disclosed in co-pending applications Ser. No. 09/073,511, filed May 6, 1998 and Ser. No. 09/102,243 filed Jun. 22, 1998.

Platform 104 of this embodiment allows ligating band dispenser 100a to move from a retracted position to an extended position to improve the field of view from and mobility of an insertion tip 16 of a hosting endoscope 10. Importantly, platform 104 is operationally transparent to the dispensing operations of these ligating band dispensers. Specifically, platform 104 accommodates the respective means for dispensing ligating bands (e.g., system push rods, rotary dispensing systems, individual band filaments) of the different ligating band dispensers to enable traditional operation of these devices.

Platform 104 of this embodiment may incorporate actuating mechanisms, including controller 150 and actuating elements 200 (e.g., actuating filaments, pneumatic systems, hydraulic systems, etc.) in accordance with the examples set forth above.

Providing an example of the operation of the present invention, reference will be made to a dispenser 100 having features illustrated in FIGS. 6a, 6c, and 6d, including proximally-biased spring 206 and actuating filaments 200d, 200e.

Dispenser 100 is positioned on the insertion tip 16 of a hosting endoscope 10. Actuating filaments 200 are passed through the work channel of the hosting endoscope 10 and through inlet 28 to the endoscope control portion 12. Actuating filaments 200 are coupled to, for example, controller 150.

For the purpose of this example, dispenser 100 begins in a retracted position. Insertion tip 16 is inserted into a patient, for example, through the mouth, to observe certain internal regions. Dispenser 100 remains in a retracted position during travel of the insertion tip 16 so as to provide the user the broadest field of view detectable by the endoscope image sensing device. Once tissue has been targeted for ligation, the user requests extension of dispenser 100. Controller 150 applies a proximally-directed force to actuating filament 200d for a predetermined time causing dispenser 100 to be extended, thus creating volume 112 defined by the interior surface of sleeve 104. After extension, opening 111 is positioned adjacent to the targeted tissue. The user applies a suction to the appropriate insertion tip 16 outlet, drawing the targeted tissue into volume 112.

The user then requests dispersal of a single ligating band 110a. If ligating band 110a was not loaded by the previous control of actuating filament 200d, controller 150 applies a proximally-directed force to actuating filament 200d for a predetermined duration causing ligating band 100a to be selected. Controller 150 then releases actuating filament 200d to apply a proximally-directed force to actuating filament 200e for a predetermined duration, thus causing ligating band 10a to be dispensed. Upon dispensing a ligating band from dispenser 100, the dispensed ligating band attempts to assume its non-expanded dimensions. As the subject tissue is positioned within an inner diameter of the ligating band, constriction of the band effectively ligates the subject tissue. The applied suction is ceased, and the insertion tip 16 moved away from the ligated tissue. If further exploration is required, actuating filaments 200d, 200e are released and spring 206 biases dispenser 100 again to a retracted position.

While the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A ligating band dispensing device having a proximal end adapted to be movably received on a distal end of an insertion portion of an endoscope, a distal end, and a sealing member adapted to move along the endoscope with movement of the dispensing device and seal a space between the dispensing device and the endoscope, wherein the dispensing device is capable of movement from a retracted position to at least a dispensing position, where for the dispensing position the distal end of the dispensing device is spaced from the distal end of the endoscope, creating a volume substantially defined by the dispensing device, sufficient to perform a ligation procedure, and in the retracted position the volume is reduced to expose the distal end of the insertion portion of the endoscope.

2. A ligating band dispensing device in accordance with claim 1, wherein the sealing member slidably engages an exterior surface of the endoscope.

3. A ligating band dispensing device in accordance with claim 1, wherein the sealing member is a rolling diaphragm.

4. A ligating band dispensing device comprising:

a ligating band dispenser adapted to be slidably mounted on a distal end of an insertion portion of an endoscope and having a proximal end, a distal end, and a sealing member to establish a seal between the dispenser and the endoscope, the sealing member having at least a portion which moves relative to the endoscope with movement of the dispenser; and an actuating mechanism, coupled to the ligating band dispenser, to selectively effect movement of the dispenser from a first position to at least a second position when coupled to the ligating band dispenser, wherein in the second position, the distal end of the dispenser is distally spaced from the distal end of the endoscope, creating a volume substantially defined by the dispenser sufficient to perform a ligation procedure, and in the first position the volume is reduced to expose the distal end of the insertion portion of the endoscope.

5. A dispensing device in accordance with claim 4, wherein the sealing member slidably engages an exterior surface of the insertion portion of the endoscope.

6. A dispensing device in accordance with claim 4, wherein the sealing member is a rolling diaphragm.

7. A dispensing device in accordance with claim 4, wherein the actuating mechanism at least partially extends along an exterior surface of the insertion portion of the endoscope.

8. A dispensing device in accordance with claim 4, wherein the actuating mechanism at least partially extends through a lumen extending through the insertion portion of the endoscope.

9. A dispensing device in accordance with claim 4, wherein the actuating mechanism has one control filament having a first end and a second end.

10. A dispensing device in accordance with claim 9, wherein the first end and the second end of the control filament are coupled to the dispenser.

11. A dispensing device in accordance with claim 9, further comprising a biasing member to bias the ligating band dispenser proximally, and the first end of the control filament is coupled to substantially the proximal end of the ligating band dispenser.

12. A dispensing device in accordance with claim 9, further comprising a biasing member to bias the ligating band dispenser distally, and the first end of the control filament is coupled to substantially the distal end of the ligating band dispenser.

13. A dispensing device in accordance with claim 4, wherein the actuating mechanism has a first filament with a connecting end and a second filament with a connecting end, and the connecting ends of the first filament and second filament are coupled to the ligating band dispenser.

14. A dispensing device in accordance with claim 13, wherein the first filament and the second filament are adapted to be positioned within a lumen extending through the insertion portion of the endoscope.

15. A dispensing device in accordance with claim 13, wherein the first filament and the second filament are adapted to be positioned along an exterior surface of the insertion portion of the endoscope.

16. A ligating band dispenser actuating device for actuating a ligating band dispenser movably mounted on a distal end of an insertion portion of a receiving endoscope from a first position to a dispensing position, the actuating device comprising an actuating mechanism adapted to be coupled to the ligating band dispenser and having at least one control filament to selectively effect the movement of the dispenser from the first position to at least the dispensing position, wherein in the dispensing position, the distal end of the dispenser is distally spaced from the distal end of the receiving endoscope, creating a volume substantially defined by the dispenser sufficient to perform a ligation procedure, and in the first position the volume is reduced to expose the distal end of the insertion portion of the endoscope.

17. An actuating device in accordance with claim 16, wherein the actuating mechanism has one control filament having a first end and a second end.

18. An actuating device in accordance with claim 17, wherein the first end and the second end of the control filament are adapted to be coupled to the dispenser.

19. An actuating device in accordance with claim 17, further comprising a biasing member to bias the ligating band dispenser distally, and the first end of the control filament is adapted to be coupled to substantially the distal end of the ligating band dispenser.

20. An actuating device in accordance with claim 17, further comprising a biasing member to bias the ligating band dispenser proximally, and the first end of the control filament is adapted to be coupled to substantially the proximal end of the ligating band dispenser.

21. An actuating device in accordance with claim 16, wherein the actuating mechanism has a first filament with a connecting end and a second filament with a connecting end, and the connecting ends of the first filament and the second filament are adapted to be coupled to the ligating band dispenser.

22. An actuating device in accordance with claim 21, wherein the first filament and the second filament are capable of being positioned within a lumen extending through the insertion portion of the receiving endoscope.

23. An actuating device in accordance with claim 21, wherein the first filament and the second filament are adapted to at least partially extend along an exterior surface of the insertion portion of the receiving endoscope.

24. A ligating band dispenser actuating device for selectively moving a ligating band dispenser, positioned on a distal end of an insertion portion of a receiving endoscope and having at least one expanded ligating band, from a retracted position to a dispensing position, the actuating device comprising:

a control portion for selectively moving the dispenser from the retracted position to at least the dispensing position; and at least one drive filament, responsive to the control portion, coupled between the control portion and the ligating band dispenser, wherein in the dispensing position, the distal end of the dispenser is distally spaced from the distal end of the receiving endoscope, creating a volume substantially defined by the dispenser sufficient to perform a ligation procedure, and in the retracted position the volume is reduced to expose the distal end of the insertion portion of the endoscope.

25. A ligating band dispenser actuating device in accordance with claim 24, wherein the control portion further includes a ligating band dispensing mechanism to selectively effect a dispensing of the at least one expanded ligating band.

26. A ligating band dispenser actuating device in accordance with claim 25, wherein the at least one drive filament includes a first drive filament to move the dispenser from the retracted position to at least the dispensing position and a second drive filament to dispense the at least one expanded ligating band from the ligating band dispenser.

27. A ligating band dispensing device comprising a ligating band dispenser adapted to be movably received on a distal end of an insertion portion of an endoscope; and an actuating mechanism, coupled to the ligating band dispenser and having at least one control filament, to selectively move the dispenser from a first position to at least a second position when coupled to the ligating band dispenser, wherein in the second position, the distal end of the dispenser is distally spaced from the distal end of the endoscope, creating a volume substantially defined by the dispenser sufficient to perform a ligation procedure, and in the first position the volume is reduced to expose the distal end of the insertion portion of the endoscope.

28. A dispensing device in accordance with claim 27, wherein the actuating mechanism has one control filament having a first end and a second end.

29. A dispensing device in accordance with claim 28, wherein the first and second ends of the control filament are coupled to the ligating band dispenser.

30. A dispensing device in accordance with claim 28, further comprising a biasing member to bias the ligating band dispenser distally, and the first end of the control filament is coupled to substantially the distal end of the ligating band dispenser.

31. A dispensing device in accordance with claim 28, further comprising a biasing member to bias the ligating band dispenser proximally, and the first end of the control filament is coupled to substantially the proximal end of the ligating band dispenser.

32. A dispensing device in accordance with claim 27, wherein the actuating mechanism has a first filament with a connecting end and a second filament with a connecting end, and the first filament and the second filament are coupled to the ligating band dispenser.

33. A dispensing device in accordance with claim 32, wherein the first filament and the second filament are capable of being positioned within a lumen extending through the insertion portion of the receiving endoscope.

34. A dispensing device in accordance with claim 32, wherein the first filament and the second filament are capable of being at least partially extending along an exterior surface of the insertion portion of the receiving endoscope.

35. A dispensing device in accordance with claim 27, further comprises a moveable platform, wherein the dispenser is fixed to the platform.

36. A ligating band dispensing device for coupling to a distal end of an insertion portion of an endoscope, the dispensing device comprising:

a ligating band dispenser supporting an expanded ligating band, the dispenser being adapted to be slidably received on the distal end of the insertion portion of the endoscope and having a sealing member to slidably engage an exterior surface of the insertion portion of the endoscope;

a control portion for selectively moving the dispenser from a first position to at least a dispensing position when the dispenser is in an operative position;

a first drive member, responsive to the control portion, coupled between the control portion and the ligating band dispenser to move the dispenser from the first position to at least the dispensing position; and an elastic retention band to fixedly engage the exterior surface of the insertion portion of the endoscope proximal to the dispenser when in an operative position, wherein in the dispensing position, the distal end of the dispenser is distally spaced from the distal end of the endoscope, creating a volume substantially defined by the dispenser sufficient to perform a ligation procedure, and in the first position the volume is reduced to expose the distal end of the insertion portion of the endoscope.

37. A ligating bank dispensing device in accordance with claim 36, wherein the retention band includes a passage extending therethrough to receive and pass the first drive member.

38. A ligating band dispensing device in accordance with claim 37, further comprising a second drive member, responsive to the control portion, coupled between the control portion and the ligating band dispenser to effect a dispensing of the expanded ligating band.

39. A ligating band dispensing device in accordance with claim 38, wherein the retention band includes at least one passage extending therethrough to receive and pass the first drive member.

40. A ligating band dispensing device in accordance with claim 39, wherein the at least one passage receives and passes the second drive member.

41. A ligating band dispensing device in accordance with claim 36, wherein the first member is proximally encompassed by a load-bearing sheath, said sheath terminating at the retention band.

42. A ligating band dispenser actuating device for actuating a ligating band dispenser, the dispenser being positioned on a distal end of an insertion portion of a receiving endoscope and having at least one expanded ligating band, from a first position to at least a dispensing position, the actuating device comprising:

a ligating band dispenser having a proximal end adapted to be movably received on a distal end of an insertion portion of a receiving endoscope, a distal end, and a sealing member adapted to move relative to the endoscope with movement of the dispensing device and seal a space between the dispensing device and the endoscope; and a controller device for selectively moving the dispenser from the first position to at least the dispensing position, wherein in the dispensing position, the distal end of the dispenser is distally spaced from the distal end of the receiving endoscope, creating a volume substantially defined by the dispenser sufficient to perform a ligation procedure, and in the first position the volume is reduced to expose the distal end of the insertion portion of the endoscope.

43. A ligating band dispenser actuating device in accordance with claim 42, wherein the controller device includes:

a user interface having at least one input element which generates a control instruction; and a controller, coupled between the at least one input element and the dispenser and responsive to the control instruction, for selectively moving the dispenser from the first position to at least the dispensing position.

44. A ligating band dispenser actuating device in accordance with claim 43, wherein the controller device further includes a dispensing controller, coupled between the at least one input element and the dispenser and responsive to the control instruction, for selectively dispensing the at least one expanded ligating band.

45. A ligating band dispenser actuating device in accordance with claim 43, wherein the controller device further includes a dispensing controller, coupled between the at least one input element and the dispenser and responsive to the control instruction, for dispensing multiple expanded ligating bands individually and sequentially.

46. A method of ligating tissue, comprising the steps of:

providing a ligating band dispenser supporting at least one expanded ligating band and positioning the dispenser on a distal end of an insertion portion of an endoscope, said ligating band dispenser being coupled to a control portion with at least one control filament for selectively moving the dispenser from a retracted position to at least a dispensing position relative to the distal end of the insertion portion;

inserting the insertion portion, including the dispenser, within a patient, wherein the dispenser is in the retracted position;

navigating the insertion portion to a desired tissue site;

adjacent to the tissue site, controlling the at least one control filament so as to extend the dispenser to at least the dispensing position, thus creating a volume substantially defined by the dispenser sufficient to receive that tissue to be ligated;

applying a suction at the distal end of the insertion portion, thus causing that tissue to be ligated to enter the volume; and dispensing a ligating band.

47. A method in accordance with claim 46, further comprising the step of:

retracting the member to the retracted position relative to the distal end of the insertion portion.

48. A method in accordance with claim 46, wherein the control portion includes a mechanism to effect the dispensing of the ligating band.

* * * * *